US011016031B2

(12) United States Patent
Olsen et al.

(10) Patent No.: US 11,016,031 B2
(45) Date of Patent: May 25, 2021

(54) BALLAST WATER ANALYSIS SYSTEM

(71) Applicant: Ballast Water Monitoring A/S, Kgs. Lyngby (DK)

(72) Inventors: Ole Olsen, Charlottenlund (DK); Kristoffer Kampmann, Gentofte (DK)

(73) Assignee: Ballast Water Monitoring A/S, Kgs. Lyngby (DK)

( * ) Notice: Subject to any disclaimer, the term of this patent is extended or adjusted under 35 U.S.C. 154(b) by 428 days.

(21) Appl. No.: 15/523,894

(22) PCT Filed: Nov. 3, 2015

(86) PCT No.: PCT/EP2015/075629
§ 371 (c)(1),
(2) Date: May 2, 2017

(87) PCT Pub. No.: WO2016/071356
PCT Pub. Date: May 12, 2016

(65) Prior Publication Data
US 2017/0350824 A1 Dec. 7, 2017

(30) Foreign Application Priority Data
Nov. 5, 2014 (EP) .................................... 14191926

(51) Int. Cl.
*G01N 21/85* (2006.01)
*G01N 21/64* (2006.01)
(Continued)

(52) U.S. Cl.
CPC ........... *G01N 21/85* (2013.01); *G01N 21/278* (2013.01); *G01N 21/49* (2013.01); *G01N 21/532* (2013.01);
(Continued)

(58) Field of Classification Search
CPC ........... G01N 33/1886; G01N 33/1893; G01N 21/532
See application file for complete search history.

(56) References Cited

U.S. PATENT DOCUMENTS 7,550,746 B2    6/2009  Tokhtuev
8,994,956 B2    3/2015  Duplisea
(Continued)

FOREIGN PATENT DOCUMENTS

DE          19930865 A1    2/2001
EP           1962089 A1    8/2008
WO   WO 2014/076171 A1    5/2014

OTHER PUBLICATIONS

"Determination of chlorophyll a using fluorimetry"; JENWAY, Bibby Scientific, Fluorimeter 6285, Application Note: A10-006A (4 pages).
(Continued)

*Primary Examiner* — William H. Beisner
(74) *Attorney, Agent, or Firm* — Nixon Peabody LLP

(57) ABSTRACT

The present invention relates in one aspect to a ballast water analysis system comprising fluorometer and light scattering meter. The fluorometer comprises a first light source arranged to illuminate a first ballast water sample for obtaining a first fluorescence measurement on a first ballast water sample. The light scattering meter comprises a second light source arranged to illuminate a second ballast water sample with a second light beam and first and second photodetectors arranged to receive light at respective angles relative to a direction of the second light beam. The second and third photodetectors are configured to receive scattered light resulting from interaction between light from the second light source and matter, such as viable or non-viable microorganisms and other particles, in the second ballast water sample.

12 Claims, 9 Drawing Sheets

(51) Int. Cl.
*G01N 21/27* (2006.01)
*G01N 21/49* (2006.01)
*G01N 21/53* (2006.01)
*G01N 33/18* (2006.01)
*G01N 21/47* (2006.01)

(52) U.S. Cl.
CPC ....... *G01N 21/645* (2013.01); *G01N 21/6456* (2013.01); *G01N 21/6486* (2013.01); *G01N 21/8507* (2013.01); *G01N 33/1886* (2013.01); *G01N 2021/4711* (2013.01)

(56) References Cited

U.S. PATENT DOCUMENTS

| | | |
|---|---|---|
| 2003/0048445 A1 | 3/2003 | Tokhtuev |
| 2007/0084990 A1 | 4/2007 | Coates |
| 2011/0246118 A1 | 10/2011 | Tokhtuev |
| 2011/0273705 A1 | 11/2011 | Rao |
| 2012/0208264 A1 | 8/2012 | Bernd |
| 2013/0107261 A1 | 5/2013 | Duplisea |
| 2014/0264077 A1 | 9/2014 | Tokhtuev |

OTHER PUBLICATIONS

Dere et al.; "Spectrophotometric Determination of Chlorophyll—A, B and Total Carotenoid Contents of Some Algae Species Using Different Solvents"; Tr. J. of Botany, 22 (1998) pp. 13-17 (5 pages).

Dubelaar, G. B. J. et al.; "Design and First Results of Cytobuoy: A Wireless Flow Cytometer for In Situ Analysis of Marine and Fresh Waters"; Cytometry, Alan Liss, New York, US; vol. 37, pp. 247-254; Aug. 17, 1999; XP002600620 (8 pages).

Bakalar, G. et al.; "Remote Monitoring of Ballast Water Treatment Quality by Using Flow Cytometry and Satellite Communication Technologie"; ELMAR; 2012 Proceedings, IEEE, Sep. 12, 2012, pp. 259-262; XP032264339 (4 pages).

McKee, D. et al.; "An integrated submersible fluorometer/nephelometer/transmissometer: design and testing at sea"; Optics & Laser Technology; Elsevier Science Publishers B.V.; vol. 29, No. 1, pp. 35-39; Feb. 1, 1997; XP004014922 (6 pages).

Poryvkina, L. et al.; "Analysis of phytoplankton pigments by excitation spectra of fluorescence"; Proceedings of EARSeL-SIG-Workship LIDAR, Dresden/FRG; Jun. 6-17, 2000, pp. 224-232 (9 pages).

Oxborough, K. et al.; "Using Fast Repitition Rate (FRR) fluorometry to monitor phytoplankton at the IMO D2 standard within ballast water discharge"; EDNS: 2271-076-PD-A; Chelsea Technologies Group Ltd., Jan. 11, 2013 (4 pages).

Price, B.J. et al.; "Light-Scatter Analysis of Microalgae—Correlation of Scatter Patterns from Pure and Mixed Asynchronous Cultures"; Biophysical Journal, vol. 22, pp. 29-36; 1978 (8 pages).

BALLAST WATER ANALYSIS SYSTEM

CROSS-REFERENCE TO RELATED APPLICATIONS

This application is a U.S. National Stage of International Application No. PCT/EP2015/075629, filed Nov. 3, 2015, which claims the benefit of European Patent Application No. 14191926.6, filed Nov. 5, 2014, both of which are incorporated herein by reference in their entireties.

The present invention relates in one aspect to a ballast water analysis system comprising fluorometer and light scattering meter. The fluorometer comprises a first light source arranged to illuminate a first ballast water sample for obtaining a first fluorescence measurement on a first ballast water sample. The light scattering meter comprises a second light source arranged to illuminate a second ballast water sample with a second light beam and first and second photodetectors arranged to receive light at respective angles relative to a direction of the second light beam. The second and third photodetectors are configured to receive scattered light resulting from interaction between light from the second light source and matter, such as viable or non-viable microorganisms and other particles, in the second ballast water sample. The ballast water analysis system may be used for the determination of presence of living phytoplankton and other particles of ballast water samples produced by on-board ballast water management systems of maritime vessels.

BACKGROUND OF THE INVENTION

Ballast water is usually loaded or taken up in port and used to stabilize a vessel or ship when the vessel has no cargo. With the uptake of ballast water follows native species of aquatic flora and fauna which are discharged with the ballast water of the vessel in a new environment when the vessel takes on cargo in a new port. Some of these organisms may survive in the sea environment at the new port and become invasive such that they presents a threat to the native ecology, the local economic activities such as fisheries or even spread diseases such as cholera.

To eliminate or at least minimize the risk of new introductions of invasive species the International Convention for the Control and Management of Ship's Ballast Water and Sediments was adopted in 2004. The Ballast Water Management Convention requires vessels in international traffic to treat their ballast water and meet certain quality criteria before discharging the water. This requirement has fueled the development of ballast water management systems (BWMS) to allow onboard treatment of the ballast water for the maritime vessels.

Certain species fluoresce and can therefore be detected based on their fluorescence. Application note A10-006A from JENWAY, discussing the "Flouorimeter 6285" discloses two methods for determining chlorophyll a in a sample by fluorimetri. In one method disclosed as the "Corrected chlorophyll a" determination, fluorescence is measured before and after acidification of the sample. A second method, "Uncorrected chlorophyll a" determination, is also disclosed.

In Proceedings of EARSeL-SIG-Workshop LIDAR, Dresden/FRG, 16-17 Jun. 2000, Poryvkina et al. disclose analysis of phytoplankton pigments by excitation spectra of fluorescence. The focus is to correctly predict pigment concentrations by use of fluorescence data.

US Patent Application Publication US 21012/0208264 A1 discloses a method and an apparatus for detecting living phytoplankton cells and/or microorganisms in or out of water, particularly ballast water, bodies of water, sewage, or water in swimming and bathing devices. The method is characterized by the following steps: variable fluorescence (Fv) is calculated by forming the difference between maximum fluorescence (Fm) and minimum fluorescence (Fo) in a measuring space or detecting part or all of the dynamic shape of a fluorescence induction curve in a measuring space, particularly measuring; and calculating the number of living phytoplankton cells and/or microorganisms of a reference species in the measuring space in accordance with the variable fluorescence (Fv).

Prior art methods are somewhat involved, and a simpler yet more powerful approach to determining presence of living microorganisms in ballast water is desirable.

SUMMARY OF THE INVENTION

A first aspect of the invention provides a ballast water analysis system comprising:
a fluorometer comprising:
a first light source arranged to illuminate a first ballast water sample and
a first photodetector arranged to receive fluorescence emitted from the first water-based sample upon illumination by the first light source for obtaining a first fluorescence measurement on the first ballast water sample. The ballast water analysis system further comprises a light scattering meter comprising:
a second light source arranged to illuminate a second ballast water sample with a second light beam,
a second photodetector arranged to receive light at a first angle $\theta_1$ with respect to a direction of the second light beam,
a third photodetector arranged to receive light at a second angle $\theta_2$ with respect to a direction of the second light beam (103), wherein the second angle $\theta_2$ is different from the first angle $\theta_1$. The second and third photodetectors are configured to receive scattered light resulting from interaction between light from the second light source and matter, such as viable or non-viable microorganisms and other particles, in the second ballast water sample. The ballast water analysis system comprises a digital controller operably coupled to the fluorometer and to the light scattering meter to receive the first fluorescence measurement and the first light scattering measurement.

The skilled person will understand that the first fluorescence measurement may provide useful information about a presence of fluorescing particles such as algae and phytoplankton in the first and second ballast water samples. However, such measurement does not necessarily provide an accurate picture of the actual content of microorganisms, viable or non-viable (dead). In combination with the scattering measurements performed by the light scattering meter it is on the other hand possible to determine with high precision the concentrations of viable microorganisms and in some cases also other particles, such as sediment.

The ballast water analysis system may comprise a digital processor to perform the actual determination of the concentrations of the viable microorganisms and possibly other particles. Accordingly, some embodiments comprises a digital processor for determining a degree of presence of viable microorganisms in the first and/or second ballast water sample(s), the determining being based on a) fluorescence measurements and corresponding light scattering measurements performed on a set of ballast water calibration samples having different concentrations of viable microorganisms, and b) the first fluorescence measurement and the first light scattering measurement.

The digital controller and the digital processor can be integrated, so that one digital processor performs both the controlling and the determination. The digital controller and the digital processor may comprise a software programmable microprocessor.

The degree of presence may be represented by a concentration or by a number or some other equivalent entity. A concentration is preferable as degree of presence, since the latter entity is most easily interpreted.

In some embodiments, the set of ballast water calibration samples also comprise calibration samples having different concentrations of non-viable microorganisms and/or sediment particles. This furthermore allows a degree of presence of non-viable microorganisms and/or sediment particles to be determined.

The first angle, characterising the arrangement of the second photodetector (112) relative to the direction of the second light beam, preferably lies in the interval 0.5-45 degrees, such as in the interval 0.5-30 degrees, such as in the interval 2-15 degrees, such as in the interval 2-10 degrees, such as in the interval 4-6 degrees. The second angle, expressing the angular location of the third photodetector relative to the direction of the second light beam, is preferably different from the first angle. In some embodiments of the present ballast water analysis system, the second angle is 0 degree, or substantially 0 degree. In some alternative embodiments, the second angle $\theta_2$ lies in the interval 1-45 degrees, such as in the interval 1-30 degrees, such as in the interval 2-30 degrees, such as in the interval 10-30 degrees, such as in the interval 20-30 degrees.

The second light source preferably comprises a laser such that the second light beam is a laser beam of light. The laser beam is a focused intense beam that can efficiently illuminate the second ballast water sample and provide reasonable scattered light intensities for the first and second photodetectors.

The first light source preferably comprises one or more LED light sources. The first light source may comprise at least one LED light source having a peak intensity in the wavelength interval 420-480 nm. LED light sources emitting light at 435 nm or 461 nm are particularly efficient for application in the first light source because of the absorption spectrum of algae and phytoplankton. With two LED light sources, one LED emitting light at 435 nm and the second emitting light at 461 nm. LEDs generally have relatively broad light spectra, so the choice, although important, is not critical to the operation of the present ballast water analysis system. However, the efficiency of the system is greatly improved by using a first light source which has a light emission spectrum that matches the known absorption spectra of algae and phytoplankton.

The first photodetector may be placed in a position outside a direct direction of a first light beam emitted by the first light source for example at an angle of substantially 90 degrees, i.e. orthogonally, relative to the direct direction of the first light beam. These orientations of the first photodetector relative to the first light beam serve to reduce the amount of light emitted by the first light source, e.g. one or more LEDs, that hits the first photodetector.

The light scattering meter of the present ballast water analysis system may comprise a fourth photodetector arranged to receive light at a third angle relative to the direction of the second light beam. The third angle is preferably different from the first angle and different from the second angle. Such difference between the angular location of the fourth photodetector and any of the second and third photodetectors ensures that the fourth photodetector provides substantially more information about the scattered light resulting from the interaction between the light of the second light source and the presence of viable or non-viable microorganisms and other particles of the second ballast water sample.

In some embodiments of the ballast water analysis system, the fluorometer, the light scattering meter, the digital controller and a power source, for powering the fluorometer, the light scattering meter and the digital controller are encapsulated in a common housing such as a waterproof housing. If the housing is water-proof, the ballast water analysis system can be operational even when submerged in the ballast water to be analyzed as discussed in further detail below with reference to the appended drawings.

In certain embodiments, the first and second ballast water samples could reasonably be considered a single ballast water sample of ballast water flowing through a test space of conduit of the ballast water analysis system as discussed in further detail below with reference to the appended drawings.

In some embodiments, the ballast water analysis system comprises a wireless transmitter unit configured to transmit to a receiver unit fluorescence measurements obtained by the fluorometer and light scattering measurements obtained by the light scattering meter. When the ballast water analysis system is submerged, a built-in transmitter can relay data to a receiver.

Some embodiments of the ballast water analysis system furthermore comprise an electronic memory for storing information representing the fluorescence measurements and corresponding light scattering measurements performed on the set of ballast water calibration samples. The ballast water analysis system furthermore comprises a digital processor for determining a degree of presence of viable microorganisms in the first or second ballast water sample, the determining being based on said stored information in the electronic memory and on the first fluorescence measurement and the first light scattering measurement, and a wireless transmitter unit configured to transmit data representing the determined degree of presence to a receiver unit.

In this embodiment, the transmission of the data is not necessarily the measurements themselves, but can be actual determined or computed concentrations of viable microorganism as determined by the digital processor. This has the further advantage that the transmitted data can be specifically related to a geometry of the housing of the ballast water analysis system and the respective location of the first and second light sources, detectors etc. In this manner, an analysis of a ballast water sample can be directly referenced to the calibration information held in the electronic memory. In other words, the ballast water calibration samples have been measured by the same, or at least similar, ballast water analysis system as the one utilized for the actual ballast water measurements during normal operation of the ballast water analysis system.

A second aspect of the invention provides a method of determining a presence of viable microorganisms in a ballast water sample, the method comprising:

obtaining a first fluorescence measurement on a first ballast water sample by illuminating the first ballast water sample by a first light source, obtaining a first light scattering measurement of a second ballast water sample by illuminating the second ballast water sample with a second light beam; and determining a degree of presence of living phytoplankton in the first or second ballast water sample, the determining being based on a) fluorescence measurements and corresponding light scattering measurements performed on a set of ballast water calibration samples having different concentrations of viable microorganisms, and b) the first fluorescence measurement and the first light scattering measurement.

The various elements and features of the ballast water analysis system described above can be used in the present method of determining the presence of viable microorganisms in ways that, in light of the present disclosure, provides the optimal performance. For instance, in some embodiments, a transmitter transmits first fluorescence measurement or first light scattering measurement to a receiver unit, or transmits determined concentrations to a receiver unit.

A third aspect of the invention relates to a ballast water management systems (BWMS) for onboard treatment of ballast water of maritime vessels. The BWMS comprises:

a ballast water flow conduit or pipe comprising an inlet section leading ballast water into a ballast water treatment apparatus and an outlet section arranged after the ballast water treatment apparatus to receive treated ballast water discharged from the ballast water treatment apparatus. The BWMS furthermore comprises a first ballast water analysis system according to any of the above-described embodiments thereof arranged in, or at, the inlet section of the ballast water flow conduit and a second ballast water analysis system according to any of the above-described embodiments thereof arranged in, or at, the outlet section of the ballast water flow conduit.

The first ballast water analysis system may be configured to analyze a first, e.g. incoming, ballast water sample using the mechanisms discussed above and generate the fluorescence measurements and light scattering measurements pertinent to the first ballast water sample. The first ballast water sample may therefore comprise unprocessed ballast water loaded from the sea surrounding the vessel carrying the BWMS. The second ballast water analysis system may be configured to analyze a second, e.g. outgoing, ballast water sample following the mechanisms discussed above and generate the above-discussed fluorescence measurements and light scattering measurements pertinent to the second ballast water sample. The second ballast water sample may comprise filtered and/or disinfected ballast water due to the operation of the ballast water treatment apparatus. The fluorescence measurements and light scattering measurements performed before and after the ballast water treatment apparatus may be used to monitor and confirm proper operation of the ballast water treatment apparatus as discussed below with the reference to the appended drawings. Constructional and operational details of the BWMS and associated advantages are discussed below in further detail with reference to FIG. 13.

One embodiment of the BWMS comprises a processor, e.g. a software programmable microprocessor, operatively connected to the first ballast water analysis system and the second ballast water analysis system via at least one data communication interface. The processor is configured to receive a first set of measured particle data from the digital controller of the first ballast water analysis system and receive a second set of measured particle data from the digital controller of the second ballast water analysis system.

Each of the first and second sets of measured particle data may comprises particle data related to one or more of:

concentrations of viable microorganisms, non-viable microorganisms, sediment particles

DETAILED DESCRIPTION OF EMBODIMENTS

Figure 1:
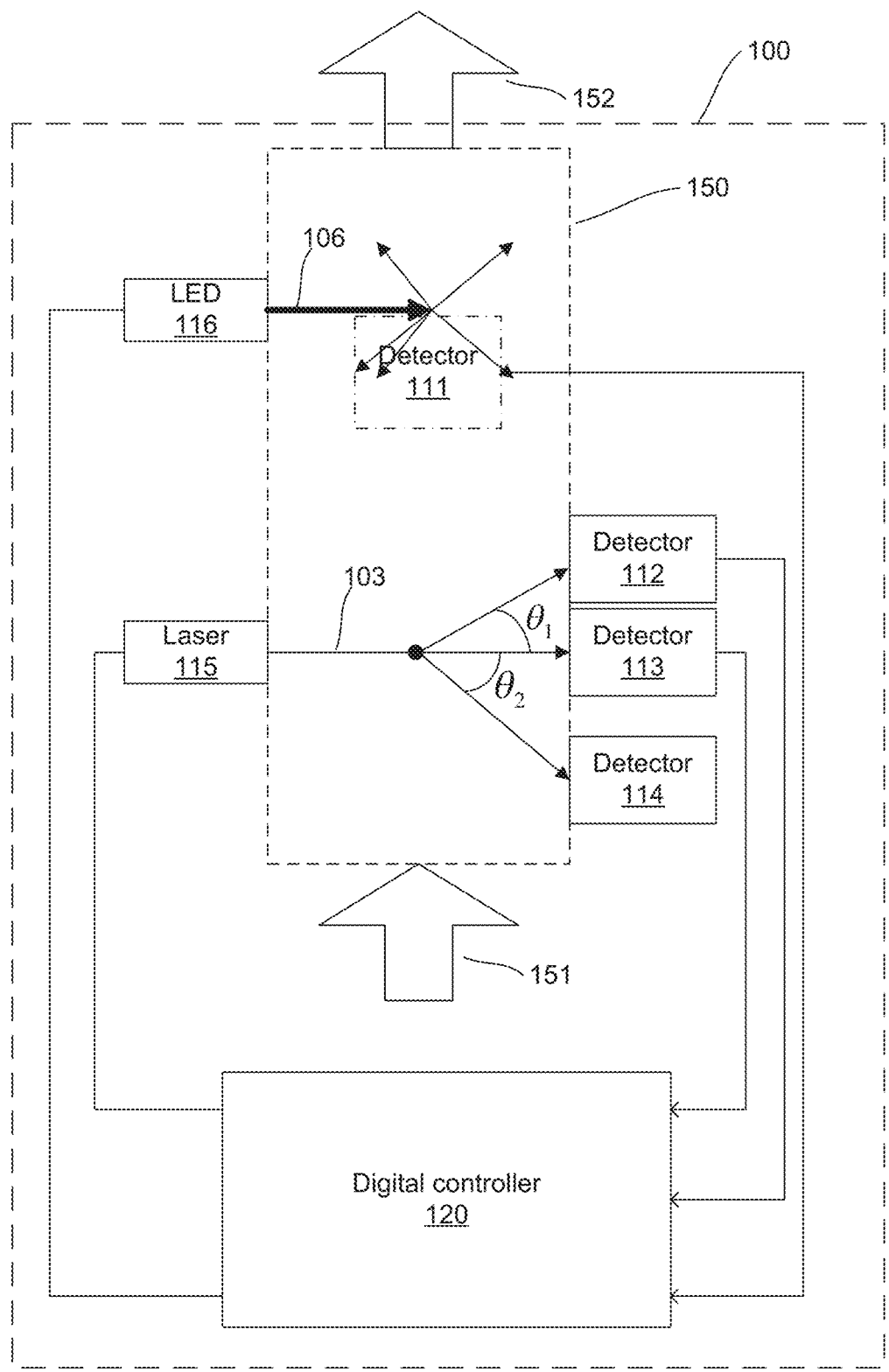
FIG. 1 illustrates a ballast water analysis system in accordance with a first embodiment of the invention.

FIG. 1 illustrates a first embodiment of the present ballast water analysis system 100. The ballast water analysis system 100 comprises a fluorometer which comprises an light-emitting diode (LED) light source 116 and a fluorescence detector 111. A digital controller 120 causes the LED light source to illuminate a first ballast water sample when located in the vicinity of the LED light source and the fluorescence detector and causes the detector 111 to perform a measurement of resulting fluorescence from the sample. This completes a fluorescence measurement, and the result is stored in the digital controller for use in determining for instance algae content in the sample.

The ballast water analysis system furthermore comprises a light scattering meter for obtaining a light scattering measurement. The light scattering meter comprises a laser light source 115 and one or more detectors such as one or more photosensitive detectors. The embodiment illustrated on FIG. 1 preferably uses three photosensitive detectors 112, 113, 114 arranged at different angles with respect to the direction of the laser beam 103. The light scattering meter preferably comprises at least two photosensitive detectors arranged at different angles relative to the direction of the laser beam 103. In the present embodiment, a first photodetector 113 of the light scattering meter (i.e. a second photo detector of the ballast water analysis system 100) is arranged in the direction of the laser beam 103 emitted by the laser source 115. Hence, the first photodetector 113 is arranged at an angle of 0 degree, or centered, relative to the direction of the laser beam 103. However, alternative embodiments of the light scattering meter may lack a photo detector at the 0 degree direction of the laser beam 103, and exclusive comprise two or more photo detectors arranged off-center and preferably at different angles. A second photo detector 112 of the light scattering meter is placed at an angle $\theta_1$ with respect to the direction of the laser beam 103. In the measurement results shown below, the second detector 112 is placed at $\theta_1=5$ degrees with respect to the direction of the laser beam 103. A third light scattering detector or photo detector 114 of the light scattering meter is located at an angle $\theta_2$ of 25 degrees with respect to the direction of the laser beam 103. The digital controller 120 may be integrally formed with the light scattering meter for example within a common housing. The digital controller 120 is configured to controlling light emission from the laser 115 and the detection of scattered light in each of the three photo detectors 112, 113, 114. The digital controller 120 causes the laser light source 115 to illuminate the water-based sample with the laser beam 103 when located in the vicinity of the laser light source and the light scattering detectors 112, 113, 114. The emission of the laser light beam 103 causes the photo detectors 112, 113, 114 to measure light scattered in the three different directions. The results of the measurement of scattered at the three photo detectors 112, 113, 114 are stored in the digital controller 120 together with the fluorescence measurement for use in determining the algae content in the ballast water sample. The data storing can also be in a separate storage element or device, but this is a matter of design.

The ballast water sample may be held in a closed container or the ballast water sample could be flowing through a particular section of a ballast water pipe, conduit or a test space, illustrated schematically as region 150 in FIG. 1 which the ballast water analysis system 100 surrounds. Alternatively, the ballast water analysis system 100 may be immersed into the ballast water pipe, conduit or a test space. The ballast water analysis system 100 may be configured to perform fluorescence and light scattering measurements on essentially the same ballast water sample or the system 100 may alternatively perform one type of measurement, such as the fluorescence measurement or the light scattering measurement, on a first ballast sample 151 when in the effective area of the fluorometer or light scattering meter, and the other measurement on another, or second, ballast water sample 152 when in the effective area of the fluorometer or light scattering meter. This increases the flexibility of the ballast water analysis system 100, since there is no strict timing requirement for the two measurements. The only requirement is that the first and second ballast water samples 151, 152 are essentially identical in terms of properties such as microorganisms (algae, phytoplankton etc.) and other particle content, such as sediment. When the ballast water samples 151, 152 are moving or flowing relative to the water analysis system (in other words moving relative to the light sources and detectors), the abovementioned flexibility is very convenient. In the latter situation, the first and second ballast water samples 151, 152 could reasonably considering a single ballast water sample of ballast water flowing through the ballast water analysis system 100. As an alternative to measuring at different times, the light scattering and fluorescence measurements can be performed simultaneously: The fluorescence measurement is performed at one place along the water conduit 150, and the light scattering measurement is performed at another place along the water conduit 150. This measurement procedure is valid under the usually very safe assumption that microorganisms and particles are uniformly distributed throughout the water sample, which means that the fluorescence measurement and the light scattering measurement are performed on two different ballast water samples, but samples having virtually identical concentrations of microorganisms and/or other particles.

Light Scattering Measurement

In one embodiment, the laser light source is a 650-nm laser. When a pipe or tube or other conduit carries the water, or a container in which the water-based sample might be still, light may for instance be transmitted into the water sample at a substantially right angle relative to the direction of the flow of water. If reflection of light back into the laser is a problem, the laser may be angled relative an interfering reflecting surface. Scattered laser light is usually not a problem. If back-reflection occurs in the setup, angling the laser may mitigate the problem.

On the opposite side of the conduit or container, transmitted light is detected in the three detectors 112, 113, 114.

The International Maritime Organization (IMO) has established limit values for certain size classes of microorganisms as the discharge standard for ballast water and the size range of $\geq 10$ μm-50 μm is dominated by phytoplankton. The discharge results from filtration of ballast water through a filtration unit. In the compliance measurement of ballast water treatment, the evaluation of the filtration unit in the ballast water compliance is therefore of great importance. Based on this information, the light scattering meter is preferably calibrated to a reference particle size standard in such a way that particle sizes in the range of 10 μm-100 μm are determined.

The signature from living algae, dead algae and other particles are different for different measurement types. The present invention relies on the realization by the inventors that a fluorescence measurement in combination with a light scattering measurement can provide much more information than the measurements provide when considered independently.

The laser light is scattered to some extent by the water-based sample. The extent depends in part on the concentration of particles in the water sample. Ballast water typically contains many types of particles, including for instance viable and non-viable (dead) microorganisms, such as algae and phytoplankton, and sand particles. These all contribute to the light scattering. The intensity of light at the three detectors strongly depends on the concentration and type of these particles.

Fluorescence Measurement

Fluorescence measurements provide information for instance about viable phytoplankton, since these fluoresce under certain illumination conditions. As described above, US patent application publication US 2012/0208264 A1 discloses a method and apparatus for detecting living phytoplankton cell and/or microorganisms in or out of water, particularly ballast water. The method is characterized by the following steps: a variable fluorescence (Fv) is calculated by forming the difference between maximum fluorescence (Fm) and minimum fluorescence (Fo) in a measuring space or detecting part or all of the dynamic shape of a fluorescence induction curve in a measuring space, particularly measuring; and calculating the number of living phytoplankton cells and/or microorganisms of a reference species in the measuring space in accordance with the variable fluorescence (Fv). It is disclosed that the variable fluorescence is a measure of the number of living phytoplankton cells and/or microorganisms in the measurement space. This is a well-established relationship.

However, not only does this prior art document not disclose the combination of fluorescence measurements with light scattering measurements. The fluorescence measurement in the present invention is also performed differently.

US 2012/0208264 A1 relies on "dark adaptation". The minimum fluorescence is measured by first dark-adapting the algae. This causes them to produce neither significant heat, nor perform photosynthesis. Then, a weak light source is used to excite carriers in the algae. The light is sufficiently weak that photosynthesis is still absent, whereas fluorescence can proceed. The result is a "minimum fluorescence", F0. A "maximum fluorescence" is measured by exposing the algae to very intense light, enough to saturate the PSII centers in the algae. This process can be assisted exposing the first water sample to light with a frequency above 700 nm. The process causes the fluorescence to be the dominating path for relaxation, and thus yields the "maximum fluorescence", Fmax.

In contrast to this method, the present invention does not rely on the minimum and maximum fluorescence values defined in US 2012/0208264 A1.

Rather, to determine the content of living and dead algae, fluorescence measurements are taken at two different excitation levels, I1 and I2, and dark-adaptation is not required. No attempt is made to suppress certain relaxation processes. In other words, for the present invention, the water sample needs not be dark adapted in advance, since a "minimum fluorescence" value is not sought. Instead, excitation with intensity I1 results in a first fluorescence signal F1, and excitation with intensity I2 higher than I1 results in a second fluorescence signal F2.

The fluorescence can be measured for instance as follows:

Excitation light is produced by an LED light source (optionally consisting of more than one individual LED light source) that emits a substantial part of its energy around 430 nm. Alternatively, the wavelength could be 460 nm. In some embodiments, two LEDs are used to increase light absorption in the algae. The light sources are operated at the same time with a pulsed current at a frequency of 8 kHz and a 50% duty cycle. In the results presented here, the measurement of F1 was performed with a light intensity corresponding to an LED current of 250 mA. The current required depends on the constitution of the water analysis system. The closer the LED light sources are to the first water sample and the closer the photodetector 111 is to the first water sample, the less current is needed. This is a matter of design, as a person skilled in the art will readily recognize.

For the measurement of F2 a current of 1250 mA p-p was used (where 250 mA p-p was used for measuring F1). F1 and F2 can for instance be measured alternately, for instance in a cycle range of 10 ms to 2 sec.

To remove spurious light, the excitation light from the LED(s) can be filtered through a short pass filter, for instance SP 550 from Delta, in order to ensure that light with longer wavelengths directly from the LED does not reach the photodetector. For the detection of the fluorescence signal, one option is to use a silicon photodiode, preferably provided with an appropriate long pass filter, for instance Delta's LP 615 filter.

The first fluorescence signal, F1, may be significantly lower than the second fluorescence signal, F2, and therefore amplification might be necessary. Phase-sensitive detection provides a lower signal-to-noise ratio, and is therefore advantageous, but not required. The excitation light from the LED can act as trigger in lock-in detection, so the activation light does not give rise to a separate current in the photodetector, which would otherwise contribute a noise signal.

Upon detection, the measurement data are digitized for further processing by the digital controller (or digital processor).

Together, the fluorescence measurement data and the light scattering measurement data are ready for processing in the digital processor in order to determine the concentration of algae in the water-based sample.

Figure 2:
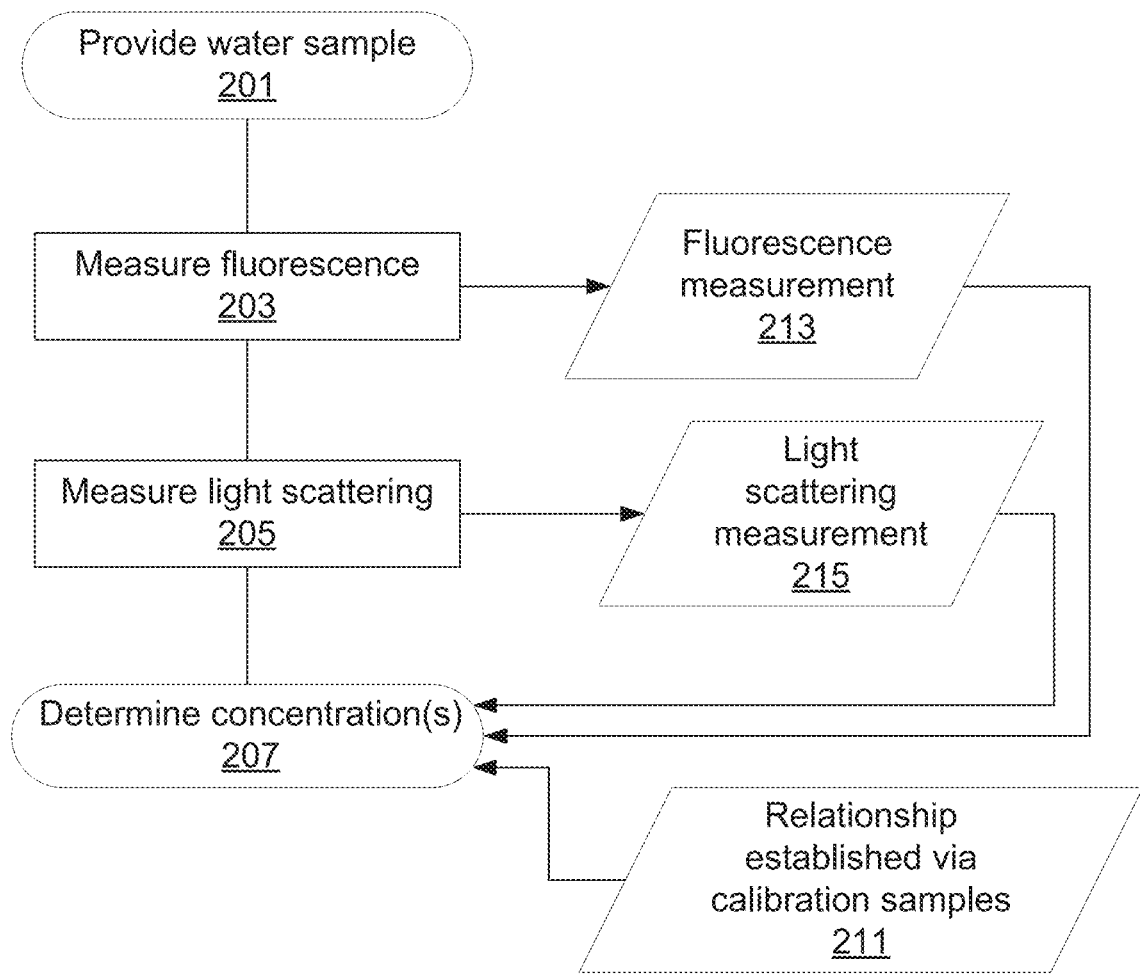
FIG. 2 illustrates a method for determining a concentration of algae in a ballast water sample.

FIG. 2 shows a flow chart of the process of determining concentrations of particles in a water sample. First step 201 is to provide the water sample. This can be done manually, where a water sample has been obtained for instance from a reservoir of standing water or from or in a pipe, tube or other conduit through which water is flowing.

Next, fluorescence and light scattering are measured on the water sample in steps 203 and 205. The order of these steps is often not of importance and can therefore be reordered if needed or desired, or be performed simultaneously. Measuring the fluorescence provides a fluorescence measurement 213, and measuring light scattering provides a light scattering measurement 215.

The method according to some embodiments of the present invention uses a relationship 211 that has been established between fluorescence measurements and light scattering measurements performed on a set of test samples with different concentrations of algae and/or other particles. As described previously, the realization that it is possible to obtain a strong correlation between these measurements is an essential element of the present invention. Based on the fluorescence measurement from step 213 and the scattering measurement from step 215, the relationship 211 is used to establish, in step 207, a concentration of algae in the water sample provided in step 201.

As described in the Summary, the invention can determine a degree of presence of living phytoplankton in a first or second water-based sample. The determining is based on a) fluorescence measurements and corresponding light scattering measurements performed on a set of water-based calibration samples having different concentrations of living phytoplankton, and b) the first fluorescence measurement and the first light scattering measurement. In order to support a correct interpretation of the determining, the following demonstrates how this can be achieved.

Figure 3:
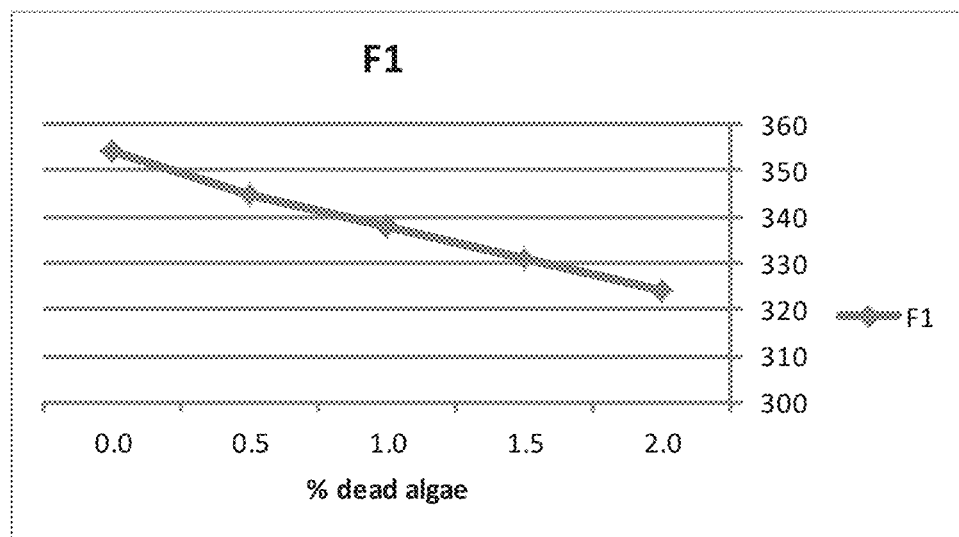
FIG. 3 shows measurements of fluorescence in a ballast water sample at two different illumination intensities.

FIG. 3 shows the results of fluorescence measurements of F1 performed on a set of water samples containing different concentrations of living algae. The intensity is in arbitrary units. As expected, the fluorescence intensity decreases as the percentage of dead algae increases. The concentration of algae is 10000/mL. Similar curves are produced (not shown) for other concentrations of algae. The result is a set of correlations between the ratio of dead-to-living algae as a function of the total concentration of algae.

Figure 4:
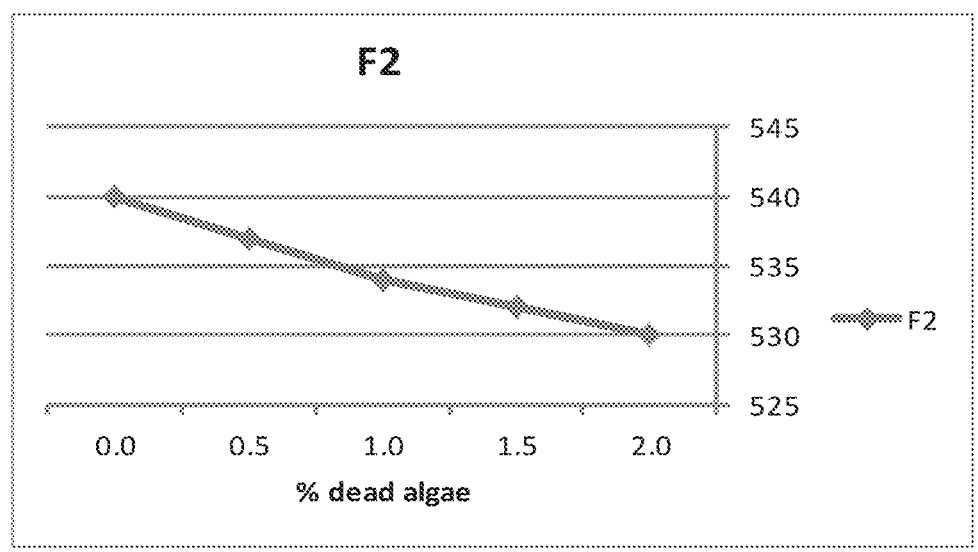
FIG. 4 shows ratios related to the results of fluorescence measurements.

FIG. 4 shows corresponding results of fluorescence measurements of F2 in the same units as the measurements in FIG. 3.

Figure 5:
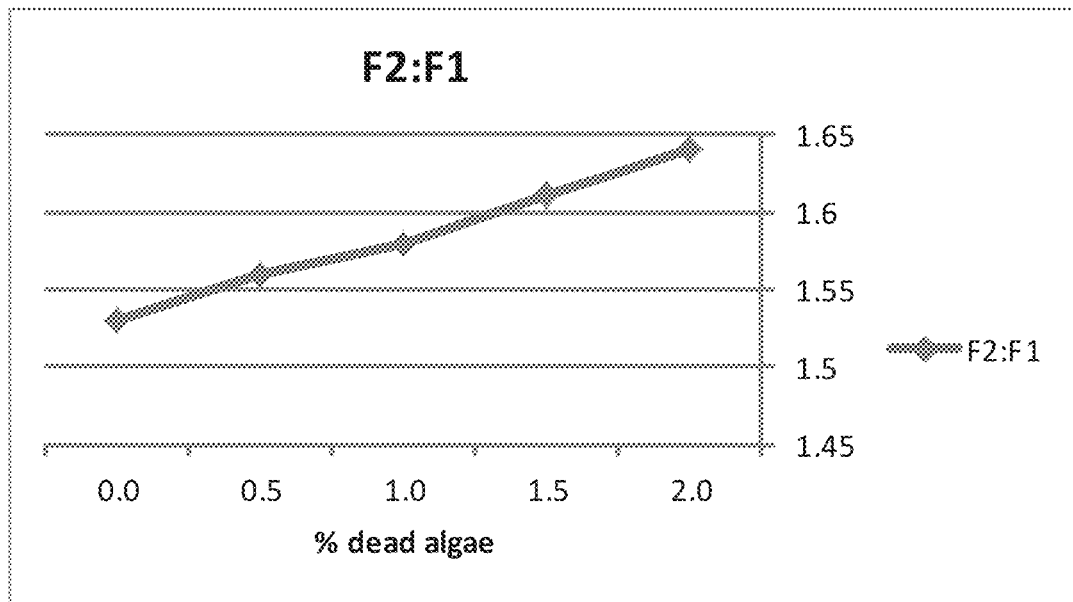
FIG. 5 shows a relationship between the ratio between dead and living algae and a representation of measured fluorescence values.

FIG. 5 shows the ratio between F2 and F1 from FIGS. 3 and 4. By considering the ratio, geometrical effects resulting from the constitution of the ballast water analysis system are removed.

Figure 6:
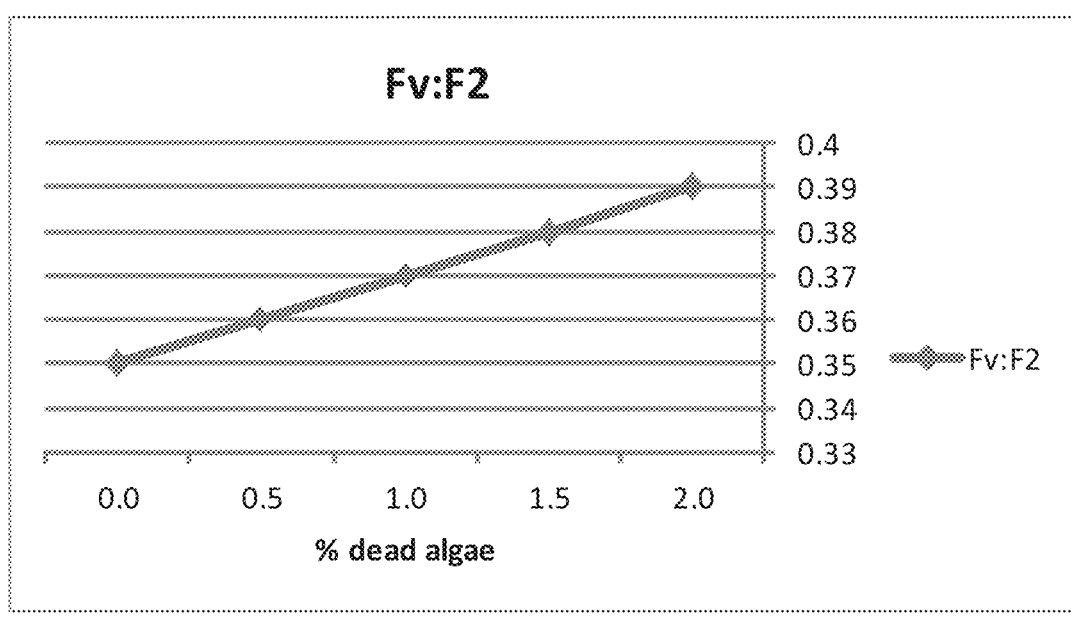
FIG. 6 shows a relationship between the ratio between dead and living algae and another representation of measured fluorescence values.

FIG. 6 shows the ratio between the second fluorescence signal and the difference fluorescence, Fv=F2−F1. There is a clear relationship with algae concentration. This relationship provides important information for use in establishing the relationship ultimately used for determining the algae concentrations in an arbitrary sample.

The use of the ratio Fv/F2 also removes effects related to the shape and type of container or conduit. Other ratios, such as for instance F2/F1 shown above, also reduce the influence of the shape and type of container or conduit, and may alternatively be used for determining the algae concentration. The exact implementation of the determination is not essential. This is a matter of design.

Figure 7:
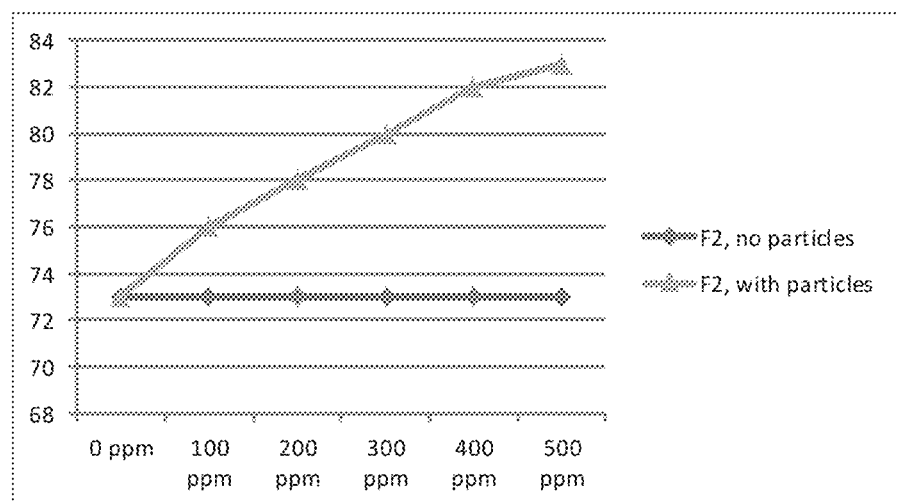
FIG. 7 shows the influence of additional particles on the fluorescence signals when the concentration of algae is 100/mL.
Figure 8:
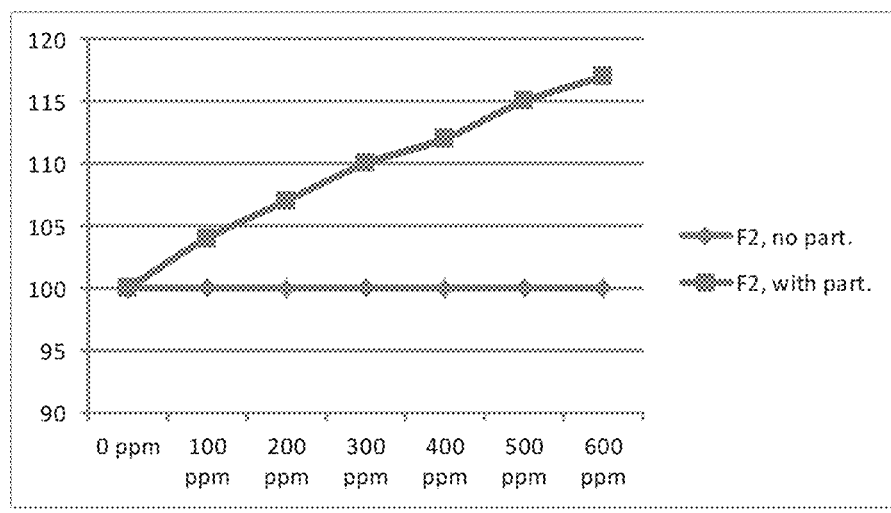
FIG. 8 shows the influence of additional particles on the fluorescence signals when the concentration of algae is 1000/mL.

The inventors also realized that F2 changes in a surprising way when particles are added. FIG. 7 shows the F2 signal as a function of additional particles. The concentration of algae is 100/mL. The baseline illustrates the expected F2 value. In reality, F2 actually increases when the concentration of additional particles increases. This type of relationship is also included when the test samples are selected, in order to be able to determine the concentration of additional particles in an actual sample. It provides crucial further information about the particle content (phytoplankton and other particles) in the samples. FIG. 8 is the same type of measurement as in FIG. 7, but the algae concentration is 1000/mL. Together, they support the determination of the concentrations of algae and additional particles in an actual sample as each contains the combined signature of fluorescing particles (phytoplankton) and non-fluorescent particles (e.g. sediment material). Further datasets will improve the precision of the determination. Furthermore, different algae species have (somewhat) different signatures, and thus sets based on different algae species can also contribute to a more precise determination of the concentrations.

Figure 9:
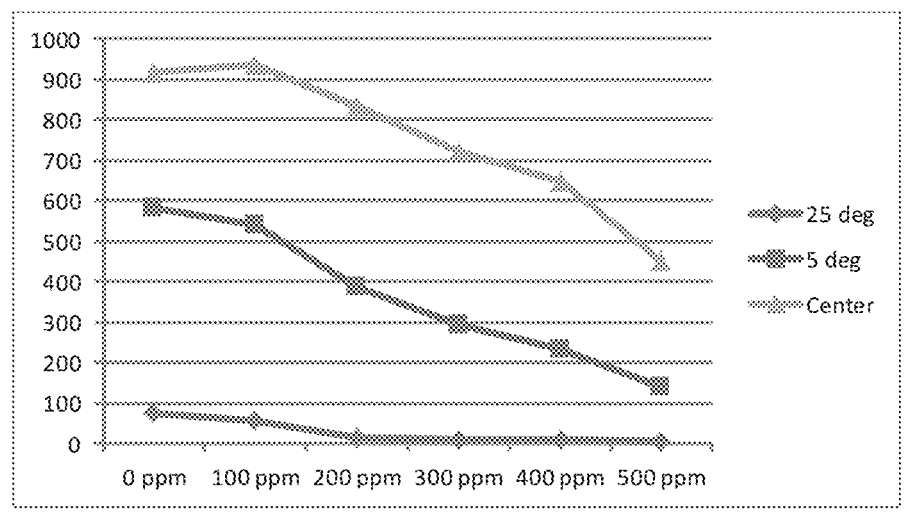
FIG. 9 shows light scattering measurements as a function of additional particles for an algae concentration of 100/mL.

The last essential component is the light scattering measurements. FIG. 9 shows the signals in the three light scattering meter detectors as a function of additional particles. The concentration of algae is 100/mL. Each detector provides a certain signal as function of additional particles. The measurements provide a number of important correlations. For instance, the ratios between the signals are in themselves a signature of the concentration of additional particles and algae. The absolute values of the signals are also important, since as the particle concentration, including both algae and non-algae, increases, the absolute signals change due to increasing scattering.

Figure 10:
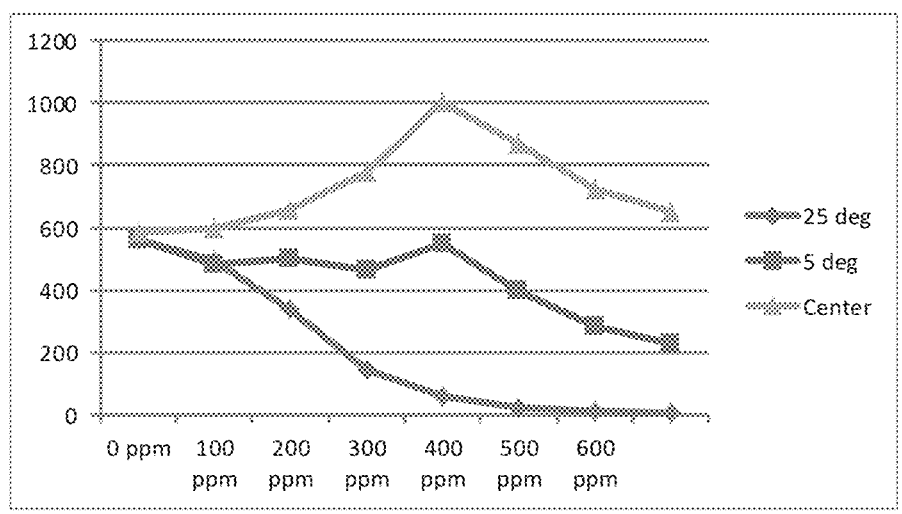
FIG. 10 shows light scattering measurements as a function of additional particles for an algae concentration of 1000/mL.

FIG. 10 is similar to FIG. 9, except for the concentration of algae which is 1000/mL. It is evident that the detector signals are very different, both in terms of the relationship between the signals and the absolute values of the individual signals. A set of such measurements again assists in providing the most precise determination of the concentrations of algae and additional particles in an actual sample.

In summary, the concentrations of algae and additional particles have a surprising influence of the fluorescence values. Thus, by establishing a set of fluorescence measurements for samples having different algae concentrations and concentrations of additional particles, valuable but not very useful information is obtained. The inventors realized that they could be combined with light scattering measurements, which provide very useful information about the concentrations of algae and additional particles. On its own, though, this information is not sufficient for actually determining the concentrations of algae and additional particles. However, in combination they can be used to very precisely determine these concentrations.

In practice, various methods can be used to actually determine the concentrations. The data may be used to establish parameterizations. Most efficient is a determination based on a lookup-and-interpolate scheme or other substantially equivalent method, where the datasets having the same signatures as that of the actual sample are determined, leading directly to the actual concentrations of algae and additional particles in the actual sample. An interpolation may be necessary as the pre-established datasets are discrete by nature.

Figure 11:
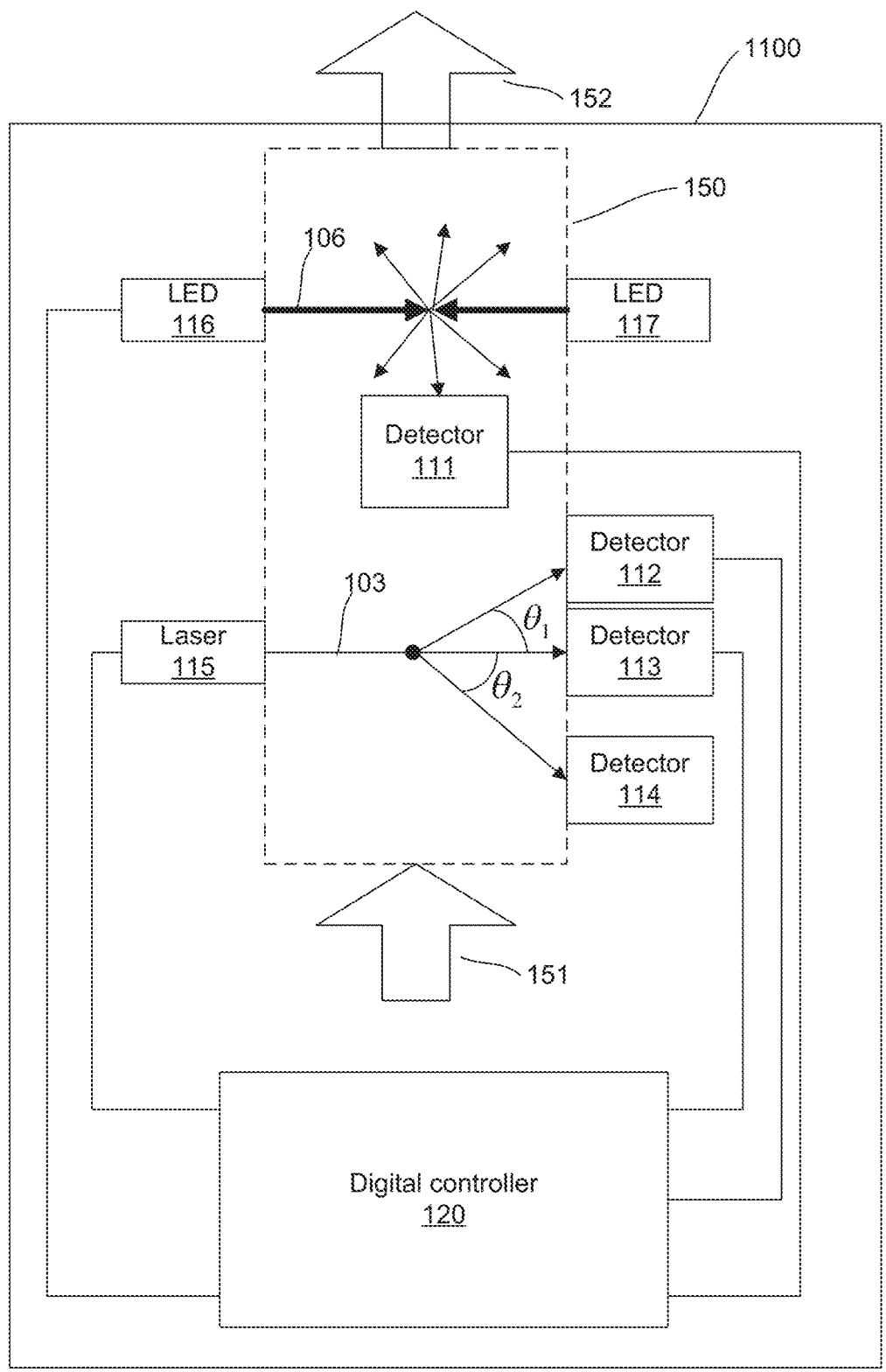
FIG. 11 illustrates a ballast water analysis system in accordance with a second embodiment of the invention.

FIG. 11 illustrates another embodiment of the ballast water analysis system. In this embodiment, the fluorometer, light scattering meter and digital controller are placed in a housing 1100 which may or may not be partially water-resistant or wholly water-resistant in order to protect these elements. Another change, which is optional, is that a second LED 117 is included and illuminates the first water-based sample. The first photodetector 111 for detecting fluorescence is located away outside the direct light path of the beam 106 emitted by the first light source to reduce the amount of light from the LEDs that enter the detector 111. The first photodetector may be placed at an angle of substantially 90 degrees, i.e. orthogonally, relative to the path or direction of the first light beam 106.

Figure 12:
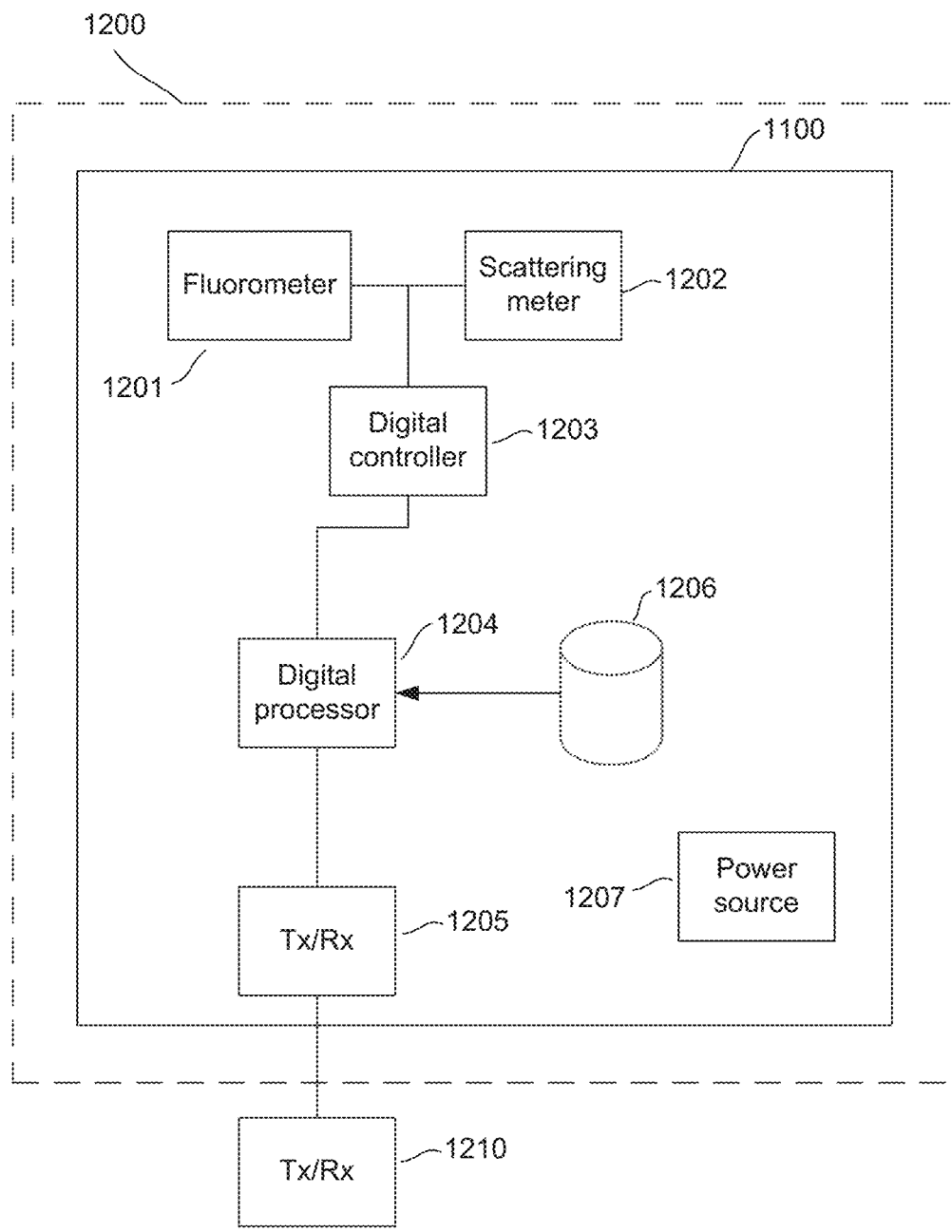
FIG. 12 illustrates illustrates a ballast water analysis system in accordance with a third embodiment of the invention.

FIG. 12 illustrates another embodiment of the ballast water analysis system. In this embodiment, a fluorometer 1201, light scattering meter 1202, digital controller 1203, digital processor 1204, an electronic memory 1206, a transmitter (and, optionally, also receiver) 1205, and a power source 1207 are positioned in a housing 1100. If the housing 1100 is water-proof, the ballast water analysis system case be submerged and operate in a volume of water. If not water-proof, the geometry of the housing is adapted to allow a water-based sample to be subjected to the fluorescence measurement and the light scattering measurement. The digital processor 1204 receives measurement results from the digital controller. The electronic memory 1206 stores information representing the fluorescence measurements and corresponding light scattering measurements performed on the set of water-based calibration samples. The information is preferably specifically related to the geometry of the housing and location of light sources, detectors etc. so that analysis of a new water-based sample in the ballast water analysis system can be directly referenced to the information in the electronic memory. Outside the ballast water analysis system, or as part of the ballast water analysis system, is a receiver unit 1210 that is configured to receive data transmitted by the transmitter 1205. The data transmitted can be concentrations determined by the processor 1204 and/or it can be the results of measurements from the fluorometer 1201 and the light scattering meter 1202. A power source 1207, such as a battery, provides power to the elements.

Figure 13:
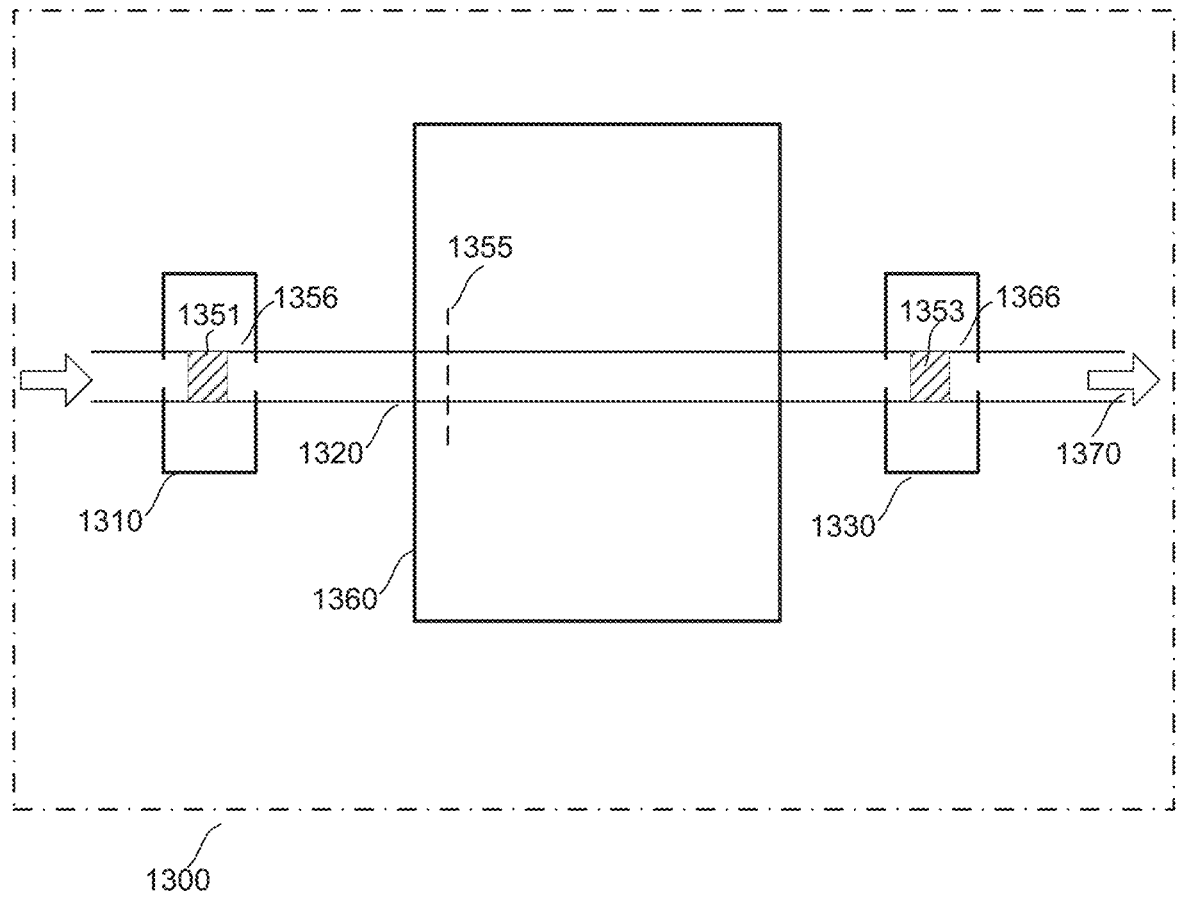
FIG. 13 illustrates schematically a ballast water management system according to another aspect of the invention.

FIG. 13 illustrates schematically a ballast water management system (BWMS) 1300 according to another aspect of the invention. The ballast water management system 1300 is well-suited for onboard treatment of ballast water of maritime vessels. The ballast water management system 1300 comprises a ballast water flow conduit or pipe 1320 comprising an inlet section 1356 leading ballast water into a ballast water treatment apparatus 1360. The water flow arrows schematically indicate the flow of ballast water through the flow conduit or pipe 1320 from the inlet section 1356, through the ballast water treatment apparatus 1360 and towards the outlet section 1366 where cleaned or rinsed ballast water is discharged. The ballast water management system 1300 comprises a first ballast water analysis system 1310 according to any of the above-described embodiments thereof arranged in, or at, the inlet section 1356 of the ballast water pipe or conduit 1320. Hence, incoming ballast water may for example flow through the previously discussed ballast water pipe, conduit or test space 150 illustrated schematically on FIG. 1. The ballast water management system 1300 comprises an additional, or second, ballast water analysis system 1330 to any of the above-described embodiments thereof arranged in, or at, the outlet section 1366 of the ballast water flow conduit 1320 in a similar manner as the first ballast water analysis system 1310.

The ballast water treatment apparatus 1360 may comprise one or more ballast water treatment devices, such as a particle filter 1355, inserted into the ballast water flow path through the treatment apparatus. The one or more ballast water treatment devices may therefore be configured to separating solids and liquids of the inflowing ballast water and/or be configured for disinfecting the inflowing ballast water by UV light or chlorine. The first ballast water analysis system 1310 is arranged before the ballast water treatment apparatus 1360 along the ballast water flow path and the second ballast water analysis system 1330 is arranged after the ballast water treatment apparatus 1360 along the ballast water flow path. The first ballast water analysis system 1310 is configured to analyze a first ballast water sample 1351 as discussed above and generate above-discussed fluorescence measurements and light scattering measurements pertinent to the first ballast water sample 1351. The first ballast water sample 1351 may be unprocessed ballast water loaded from the sea surrounding the vessel. The second ballast water analysis system 1330 is configured to analyze a second ballast water sample 1353 following the mechanisms discussed above and generate the above-discussed fluorescence measurements and light scattering measurements pertinent to the second ballast water sample 1351. The second ballast water sample 1353 may comprise filtered and/or disinfected ballast water due to the operation of the ballast water treatment apparatus 1360. This filtered and/or disinfected ballast water may be discharged into a ballast water tank (not shown) of the vessel from a termination 1370 of the ballast water flow conduit 1320.

The fluorescence measurements and light scattering measurements performed before and after the ballast water treatment apparatus 1360 may be used to monitor and confirm proper operation of the ballast water treatment apparatus 1360. The fluorescence measurements and light scattering measurements may for example be utilized to selectively determine respective concentrations of viable microorganisms, non-viable microorganisms and sediment particles in each of the first and second ballast water samples 1351, 1353, respectively. Hence, allowing a suitable application program or routine to determine the efficiency of the operation of the ballast water treatment apparatus 1360 in a detailed manner by comparing the obtained reductions of the respective concentrations of the viable microorganisms, non-viable microorganisms and sediment particles between the first and second ballast water samples 1351, 1353. The application program or routine may be configured notify an operator or technician of the BWMS 1300 if the obtained reductions of the respective concentrations of the viable microorganisms, non-viable microorganisms and sediment particles fails to meet a certain performance of quality criterion which could indicate a malfunction or suboptimal function of one or more of the ballast water treatment devices.

The first and second ballast water analysis systems 1310, 1330 may for example comprise respective wireless or wired data communication interfaces (not shown) connected to the BWMS 1300 for transmitting first and second sets of measured particle data, e.g. including one or more of the above concentrations of viable microorganisms, non-viable microorganisms and sediment particles, to a processor of the BWMS 1300. The processor of the BWMS 1300 may comprise a software programmable microprocessor executing the application program or routine discussed above and connected to various peripheral devices such as memory and a display with a suitable graphical user interface.

The invention claimed is:

1. A ballast water analysis system comprising:
   a fluorometer comprising: a first light source arranged to illuminate a first ballast water sample received in the ballast water analysis system and a first photodetector arranged to receive fluorescence emitted from the first ballast water sample upon illumination by the first light source for obtaining a first fluorescence measurement on the first ballast water sample; and
   a light scattering meter comprising: a second light source arranged to illuminate a second ballast water sample with a second light beam, a second photodetector arranged to receive light at a first angle $\theta_1$ with respect to a direction of the second light beam, wherein the first angle lies $\theta_1$ in an interval 0.5-45 degrees relative to the direction of the second light beam,
   a third photodetector arranged to receive light at a second angle $\theta_2$ with respect to a direction of the second light beam, wherein the second angle $\theta_2$ is different from the first angle $\theta_1$,
   the second and third photodetectors being configured to receive scattered light resulting from interaction between light from the second light source and matter in the second ballast water sample; and
   a digital controller operably coupled to the fluorometer and to the light scattering meter to receive the first fluorescence measurement and a light scattering measurement,
   the digital controller being configured to determine a degree of presence of viable microorganisms in at least one of the first ballast water sample or the second ballast water sample based on a) fluorescence measurements and corresponding light scattering measurements performed on a set of ballast water calibration samples having different concentrations of viable microorganisms and different concentrations of non-viable microorganisms or sediment particles, and b) the first fluorescence measurement and the light scattering measurement.

2. A ballast water analysis system according to claim 1, wherein the second angle $\theta_2$ characterising the arrangement of the third photodetector relative to the direction of the second light beam is 0 degree.

3. A ballast water analysis system according to claim 1, wherein the second angle $\theta_2$ of the third photodetector relative to the direction of the second light beam is in the interval 1-45 degrees, or in the interval 1-30 degrees, or in the interval 2-30 degrees, or in the interval 10-30 degrees, or in the interval 20-30 degrees.

4. A ballast water analysis system according to claim 1, wherein the light scattering meter furthermore comprises a fourth photodetector arranged to receive light at a third angle $0_3$ relative to the direction of the second light beam.

5. A ballast water analysis system according to claim 1, wherein the first light source comprises an LED light source having a peak intensity in the wavelength interval 420-480 nm; and/or the second light source comprises a laser.

6. A ballast water analysis system according to claim 1, wherein the first photodetector is placed in a position outside a direct direction of a first light beam emitted by the first light source at an angle of substantially 90 degrees with the respect to the direct direction of a first light beam.

7. A ballast water analysis system according to claim 1, wherein the fluorometer, the light scattering meter, the digital controller and a power source for powering the fluorometer, the light scattering meter and the digital controller are encapsulated in a common housing or a waterproof housing.

8. A ballast water analysis system according to claim 7, further comprising
electronic memory for storing information representing the fluorescence measurements and corresponding light scattering measurements performed on the set of ballast water calibration samples, and
a wireless transmitter unit configured to transmit data representing the determined degree of presence of the viable microorganisms to a receiver unit.

9. A ballast water analysis system according to claim 1, further comprising a wireless transmitter unit configured to transmit to a receiver unit fluorescence measurements obtained by the fluorometer and light scattering measurements obtained by the light scattering meter.

10. A ballast water management system (BWMS), comprising:
a ballast water flow conduit or pipe comprising an inlet section leading ballast water into a ballast water treatment apparatus and an outlet section arranged after the ballast water treatment apparatus to receive treated ballast water discharged from the ballast water treatment apparatus,
a first ballast water analysis system according to claim 1 arranged in, or at, the inlet section of the ballast water flow conduit and a second ballast water analysis system according to claim 1 arranged in, or at, the outlet section of the ballast water flow conduit.

11. A ballast water management system (BWMS) according to claim 10, comprising:
processor operatively connected to the first ballast water analysis system and the second ballast water analysis system via at least one data communication interface, wherein the processor is configured to receive a first set of measured particle data from the digital controller of the first ballast water analysis system and receive a second set of measured particle data from the digital controller of the second ballast water analysis system.

12. A ballast water management system (BWMS) according to claim 11, wherein each of the first and second sets of measured particle data comprises particle data related to one or more of:
concentrations of viable microorganisms, non-viable microorganisms, sediment particles.

* * * * *